United States Patent [19]

Photis

[11] 4,234,506
[45] Nov. 18, 1980

[54] PROCESS FOR PREPARING CYANOHYDRIN ESTERS

[75] Inventor: James M. Photis, Ridgefield, Conn.

[73] Assignee: Stauffer Chemical Company, Westport, Conn.

[21] Appl. No.: 80,955

[22] Filed: Oct. 1, 1979

[51] Int. Cl.³ .................. C07C 121/38; C07C 121/46; C07C 121/75

[52] U.S. Cl. .............................. 260/465 D; 260/464; 260/465.4

[58] Field of Search ................. 260/465 D, 464, 465.4

[56] References Cited

FOREIGN PATENT DOCUMENTS 52-142046 11/1977 Japan.

OTHER PUBLICATIONS

Cox et al., *Organic Synthesis Collective* vol. 2, p. 7 (1943).
Wagner et al., *Organic Synthesis Collective* vol. 3, p. 324 (1955).
Nasipuri et al., *J. Indian Chemical Soc.*, 44, p. 556 (1967).
Gassman et al., *Tetrahedron Letters*, pp. 3773-3776 (1978).
Umino et al., *Tetrahedron Letters* No. 33, pp. 2875-2876 (1976).
Sugimoto et al., *J. Chem. Soc. Chem. Comm.*, pp. 926-927 (1978).
Kinishi et al., *Agric. Biol. Chem.* 42 (4), pp. 869-872 (1978).
Borch et al., *J. Org. Chem.*, 37, pp. 726-729 (1972).

*Primary Examiner*—Dolph H. Torrence
*Attorney, Agent, or Firm*—William C. Gerstenzang

[57] ABSTRACT

Cyanohydrin esters are prepared by reacting an acyl cyanide represented by the structure

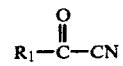

with an acyl cyanide represented by the structure

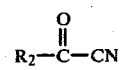

and an alkali metal borohydride.

9 Claims, No Drawings

PROCESS FOR PREPARING CYANOHYDRIN ESTERS

BACKGROUND OF THE INVENTION

The present invention relates to a novel process for the preparation of cyanohydrin esters. More particularly, the present invention relates to the preparation of cyanohydrin esters from acyl cyanides.

Cyanohydrin esters are important industrial materials both as intermediates to be used in making other compounds and as compounds having utility in and of themselves.

An example of the former is meta-phenoxybenzaldehyde cyanohydrin acetate, which is represented by the formula:

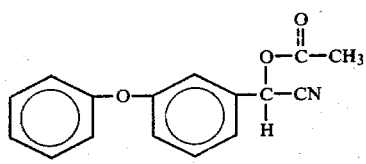
I

An example of the latter is the pyrethroid-type insecticide represented by the formula:

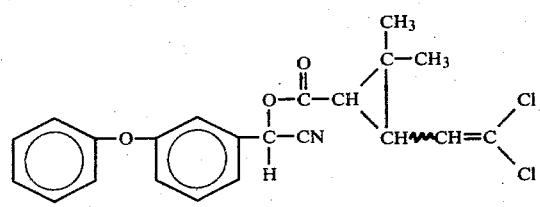
II

The compound of formula I can be used as an intermediate cyanohydrin ester from which the insecticidally-active cyanohydrin ester of formula II is prepared, as follows:

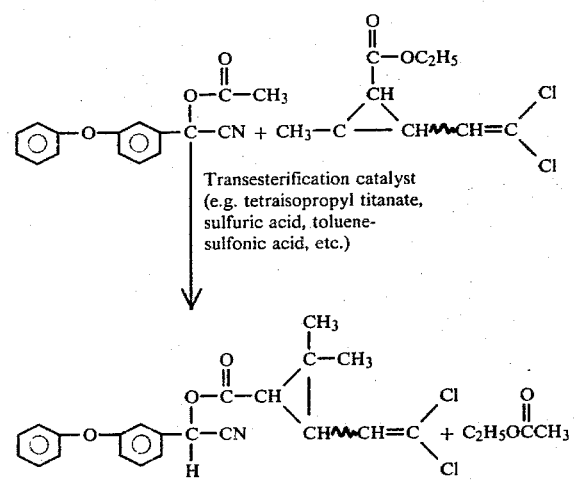

This method of preparing cyanohydrin esters of the type represented by compound II presupposes the availability of the intermediate compound I.

The intermediate cyanohydrin ester represented by formula I can be prepared by reacting a free cyanohydrin with acetic anhydride, as follows:

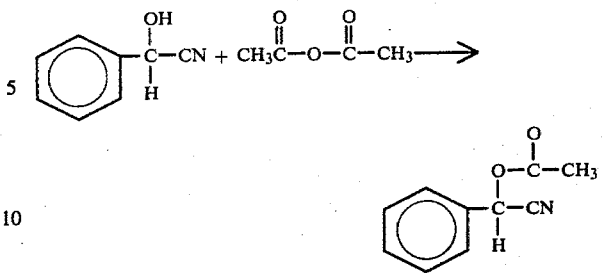

This overall method for preparing cyanohydrin esters of the type represented by formula II is not preferred for two reasons. The first is that it is a two-step process, the first step being the preparation of an intermediate cyanohydrin ester (compound I), and the second step being the further reaction of the intermediate to form the final product. The second objection is that it requires, in the first step, the handling of a free cyanohydrin. Free cyanohydrins are unstable compounds which can release HCN.

It is highly desirable therefore that a method be provided for preparing cyanohydrin esters by a one-step process which does not require the use of free cyanohydrins.

SUMMARY OF THE INVENTION

It is an object of the present invention to provide a novel one-step process in which cyanohydrin esters are prepared directly from acyl cyanides.

It has now been discovered that cyanohydrin esters can be readily prepared by the direct reduction of acyl cyanides using an alkali metal borohydride as the reducing agent. Surprisingly and unexpectedly, it has been found that when acyl cyanide is reduced by an alkali metal borohydride, only the acyl functionality is reduced, and the nitrile moiety remains intact and is not cleaved from the molecule. This is particularly surprising in view of the tendency of other reducing agents, such as lithium aluminum hydride, to also reduce the nitrile functionality and the tendency of other basic reagents, such as sodium hydroxide, to cleave the cyano group from the molecule.

In accordance with the present invention there is provided a process for preparing cyanohydrin esters represented by the formula:

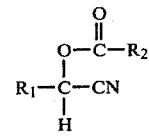

which comprises reacting at least one acyl cyanide represented by the structure:

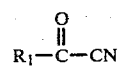

with at least one acyl cyanide represented by the structure:

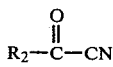

and an alkali metal borohydride.

The reaction can be conducted in an aqueous or nonaqueous medium, or in a 2-phase medium using a phase transfer technique.

When conducting the reaction in an aqueous media, a solution of the acyl cyanides in a water miscible solvent is prepared and this solution is then brought into contact with an aqueous solution of an alkali metal borohydride at a temperature and for a time sufficient to form the cyanohydrin esters. Under these conditions the reaction will proceed without the need for any catalyst.

The water miscible solvents used include, but are not limited to dioxane, tetrahydrofuran, dimethoxyethane, bis-(2-methoxyethyl)ether, bis-(2-ethoxyethyl) ether and other such polyether solvents, although dioxane is preferred.

The concentrations of acyl cyanide and alkali metal borohydride in the aqueous solution range from about 50 to about 500 grams acyl cyanide per liter of solution and from about 5 to about 100 grams alkali metal borohydride per liter of solution. At higher concentrations direct reduction of the reactants to alcohols can result, while at lower concentrations reaction rate can be slow and the desired reaction incomplete.

The solution of acyl cyanides in water miscible solvent and the aqueous solution of acyl cyanide and alkali metal borohydride are each prepared by conventional means.

The two solutions are brought into contact by mixing them together, in any order. This is to say, either solution may be added to the other. The addition of one solution to the other may be accomplished by either metering controlled amounts of each into a reaction zone on a continuous basis, or by simply pouring one into the other in batch mixing equipment.

Once the two solutions are brought together, the reaction will begin. No catalyst is required.

The reaction is mildly exothermic and external cooling may be required.

The reaction temperature should not be permitted to exceed about 50° C., and preferably should be maintained within the range of from about 20° to about 40° C. At temperatures in excess of about 50° C. direct reduction of the alkali metal cyanides to alcohols can take place to an appreciable degree, while at temperatures below about 20° C. reaction rates become relatively slow.

The essential completion of the reaction will be indicated by the disappearance of the characteristic carbonyl absorption bands in the inrared spectrum.

The reaction can generally be essentially completed in time periods ranging from about 15 minutes to about 1 hour, and conversion generally ranges from about 60% to about 100%.

Once the reaction is completed, the product cyanohydrin ester can be recovered from the reaction mass by conventional means. A preferred conventional method for recovering the product cyanohydrin ester from the aqueous reaction mass comprises adding water and a water immiscible solvent, such as methylene chloride, to the aqueous reaction mass and stirring for a time sufficient for the water-immiscible solvent to extract the cyanohydrin ester from the aqueous reaction mass; and then separating the water immiscible solvent from the reaction mass, and subsequently, the cyanohydrin ester from the water-immiscible solvent, as for example, by evaporating the solvent to leave the ester.

The reaction can also be conducted in a non-aqueous solvent in which the particular acyl cyanides being reacted are soluble. It is preferable that the solvent used be one in which the alkali metal borohydride is soluble, although even slight solubility of the alkali metal borohydride will enable the reaction to proceed. In this latter case, however, the reaction may take longer to complete than would be the case using a solvent in which the alkali metal borohydride is completely soluble.

Typical of the nonaqueous solvents in which the reaction may be conducted are isopropanol, tetrahydrofuran, diethyl ether, bis-(2-ethoxyethyl) ether, dimethoxy ethane and dioxane; although diethyl ether and tetrahydrofuran are preferred.

It should be noted that when conducting the reaction in aqueous media, a possibility exists that some of the acyl cyanide may be hydrolyzed to the corresponding alcohol. When conducting the reaction in a nonaqueous solvent, on the other hand, the reaction rate may be slower than desired because the alkali metal borohydride may not be completely soluble in the solvent. These problems can be minimized by using a two-phase media and a phase transfer catalyst.

In a preferred embodiment, therefore, the process comprises forming a mixture of the acyl cyanides and a phase transfer catalyst in an inert water-immiscible solvent; bringing the mixture into contact with an aqueous solution of an alkali metal borohydride, and maintaining the contact at a temperature and for a time sufficient to convert at least a portion of the acyl cyanides to cyanohydrin ester.

The phase transfer catalysts which are employed can be any of those which are generally used for phase-transfer reactions. These include, but are not limited to, quaternary ammonium salts which are soluble in both the aqueous and organic phases, such as
benzyl trimethyl ammonium chloride,
tetra-n-butyl ammonium bromide,
tetra-n-butyl ammonium iodide and
tetra-n-hexyl ammonium bromide;
although tetra-n-butyl ammonium bromide and tetra-n-butyl ammonium iodide are prepferred; with tetra-n-butyl ammonium bromide being most preferred. Other types of phase transfer catalysts may also be used.

The amount of phase transfer catalyst used ranges from about 0.005% to about 1.0% by weight of water-immiscible solvent used; although amounts ranging from about 0.1% to about 0.3% by weight of solvent are preferred.

There are many solvents known in the art which can be used as the inert water-immiscible solvents in the practice of the present invention. These include, but are not limited to methylene chloride and other halogenated hydrocarbons; aliphatic hydrocarbons, aromatic hydrocarbons and ether solvents; although methylene chloride is preferred.

The relative amount of solvent used is not critical but it is generally preferred that the mixtures of acyl cyanide and water-immiscible solvent contain total concentrations of acyl cyanide ranging from about 5% to about 50% by weight of mixture.

In practicing the present invention, in accordance with this embodiment, a mixture of the acyl cyanide, phase transfer catalyst and a water-immiscible solvent is formed using conventional techniques. This mixture can be prepared by bringing the components together and stirring until a uniform mixture is formed.

In a similar manner, an aqueous solution of alkali metal borohydride, containing from about 2% to about 5% alkali metal borohydride, by weight of solution, can be prepared by adding the proper amount of alkali metal borohydride to the proper amount of water and stirring until a uniform solution is formed.

The aqueous solution of alkali metal borohydride and the mixture of acyl cyanides, phase transfer catalyst and water-immiscible solvent are then brought into contact with each other under such conditions as will promote a phase transfer reaction involving the acyl cyanides, phase transfer catalyst and alkali metal borohydride. This can generally be accomplished by intimately mixing the mixture and solution to form a reaction mixture.

Once the reaction mixture is formed, the phase transfer reaction involving the acyl cyanides, alkali metal borohydride and phase transfer catalyst will take place. This reaction is exothermic and external cooling may be required.

Upon completion of the reaction the water-immiscible phase is separated from the reaction mixture, and the solvent evaporated to yield the cyanohydrin ester product.

The acyl cyanides represented by the formulae:

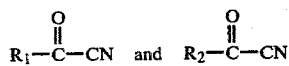

are independently selected from the group consisting of compounds represented by the general formula

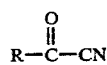

wherein R represents an alkyl, alkenyl, cycloalkyl, aryl, aralkyl, alkylphenyl, diphenyl ether, or polyphenyl radical, or a radical made up of any combination thereof; and may contain an inert substituent selected from the group consisting of halogen, alkyl and alkoxy; the radical having a total number of carbon atoms ranging from 1 to about 30.

The acyl cyanides represented by

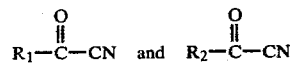

may, of course, be the same or different.

Preferably the compound represented by

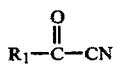

is meta-phenoxybenzoyl cyanide, i.e.;

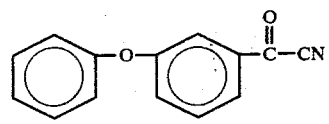

and the compound represented by the formula

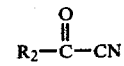

is 3-(2,2-dichlorovinyl)-2,2-dimethyl cyclopropane carboxylic acid cyanide, i.e.,

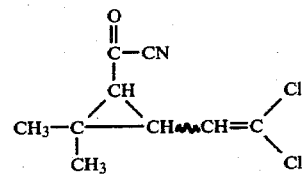

Although not critical to the practice of the present invention, it is preferred that the compounds represented by

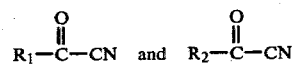

be used in equimolar quantities.

The alkali metal borohydrides used in the practice of the present invention include sodium borohydride, potassium borohydride, lithium borohydride and mixtures thereof; although sodium borohydride is preferred, because it is readily available.

It is preferred, as a matter of economy, to use about 0.25 equivalents of alkali metal borohydride based on the total amount of acyl cyanides used, since all four hydrogens in the alkali metal borohydride are active. The amount used should in no case exceed about 0.5 equivalents as amounts in excess of 0.5 equivalents can result in the formation of alcohols rather than cyanohydrin esters.

The water-immiscible phase is then separated from the reaction mixture, and the solvent evaporated to yield the cyanohydrin ester product.

In an especially preferred embodiment, the present invention comprises a process for preparing an insecticidally-active cyanohydrin ester which comprises reacting a mixture of meta-phenoxybenzoyl cyanide and 3-(2,2-dichlorovinyl)-2,2-dimethyl cyclopropane carboxylic acid cyanide with sodium borohydride by a phase transfer reaction in the presence of a phase transfer catalyst to form a cyanohydrin ester product of the meta-phenoxybenzoyl cyanide and 3-(2,2-dichlorovinyl)-2,2-dimethyl cyclopropane carboxylic acid cyanide.

This especially preferred embodiment is illustrated as follows:

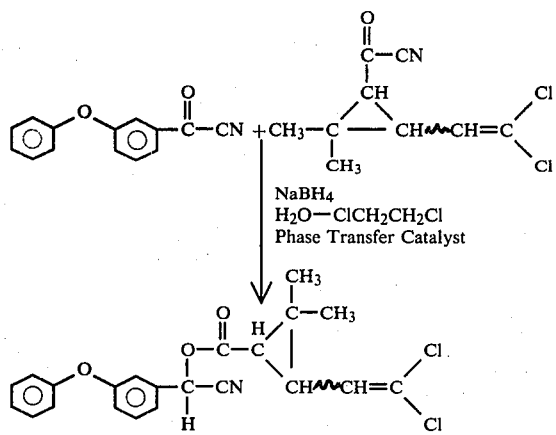

In order that the present invention be more fully understood, the following examples are given by way of illustration, no specific details or enumerations contained therein should be construed as limitations except insofar as they appear in the appended claims. All parts and percentages are be weight unless otherwise specifically designated.

EXAMPLE 1

Preparation of Meta-Tolualdehyde Cyanohydrin Meta-Toluate

A solution of 0.30 gram (7.9 moles) of sodium borohydride and 20 milligrams of tetra-n-butyl ammonium bromide in 10 milliliters of water was prepared in a magnetically stirred flask. Then a solution of 2.2 grams (15.2 moles) of meta-toluyl cyanide in 12 milliliters of methylene chloride was added to the flask.

Stirring was continued for 55 minutes, after which the flask contents were permitted to settle into two phases. The organic phase was removed and concentrated on a rotary evaporator to yield 2.00 grams (100% of theory) of an orange colored oil which was identified as the cyanohydrin ester by infrared analysis ($\nu_{c=o}$ 1730 cm$^{-1}$) and NMR $\int_{TMS}^{CDCl_3}$ 6.75

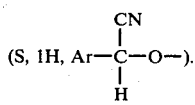

(S, 1H, Ar—C—O—).

EXAMPLE 2

Preparation of R,S-α-Cyano-3-Phenoxybenzyl (Cis, Trans)-3-(2,2-Dichlorovinyl)-2,2-Dimethylcyclopropane Carboxylate A solution of 1.09 grams (5.0 m moles) of dichlorochrysanthemyl cyanide and 1.12 grams (5.0 m mole) of meta-phenoxybenzoyl cyanide in 2.5 milliliters of methylene chloride was prepared in a magnetically stirred flask. Tetra-n-butyl ammonium chloride in the amount of 25 milligrams was then added followed by a solution of 0.060 grams (1.58 m mole) of sodium borohydride in 2 milliliters of water.

After 30 minutes an additional 0.030 gram (0.79 m mole) of sodium borohydride was added and stirring continued for an additional 20 minutes.

The flask contents were then permitted to settle into two layers. The organic layer was removed and concentrated to yield 2.1 gram (100% of theory) of a pale orange liquid which was identified as cyanohydrin ester by infrared analysis $\nu_{c=o}$ 1740 cm$^{-1}$. The product demonstrated an LD$_{50}$ against houseflies of 0.5 as compared to 0.06 for a sample of authentic R, S -α-cyano-3-phenoxybenzyl (cis, trans)-3-(2,2-dichlorovinyl)-2,2-dimethylcyclopropane carboxylate.

The difference between the insecticidal activity of the product and the authentic material is attributed to the dilution of the product by the presence therein of other products of the reaction.

It will thus be seen that the present invention provides a process by which cyanohydrin esters can be prepared directly from acyl cyanides.

The objects set forth above, among those made apparent from the preceding description are, therefore, effectively attained and, since certain changes may be made in the above method without departure from the scope of the invention, it is intended that all matter contained in the above description shall be interpreted as illustrative and not in a limiting sense.

What is claimed is:

1. A process for preparing cyanohydrin esters represented by the formula:

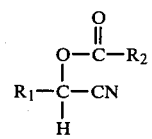

which comprises reacting at least one acyl cyanide represented by the structure

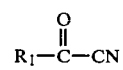

with an alkali metal borohydride and at least one acyl cyanide represented by the structure:

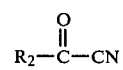

wherein R$_1$ and R$_2$ can be the same or different and each independently represents alkyl, alkenyl, cycloalkyl, aryl, aralalkyl, alkylphenyl, diphenyl ether, or polyphenyl radical, or a radical made up of any combination thereof; and may contain an inert substituent selected from the group consisting of halogen, alkyl and alkoxy; the radical having a total number of carbon atoms ranging from 1 to about 30.

2. The method of claim 1 wherein said alkali metal borohydride is selected from the group consisting of sodium borohydride, potassium borohydride, lithium borohydride and mixtures thereof.

3. The method of claim 2 wherein said alkali metal borohydride is sodium borohydride.

4. The method of claim 3 wherein said acyl cyanide represented by the structural formula:

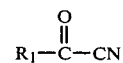

is meta-phenoxybenzyl cyanide, and said acyl cyanide represented by the structural formula:

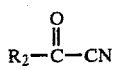

is 3-(2,2-dichlorovinyl)-2,2-dimethyl cyclopropane carboxylic acid cyanide.

5. The method of claim 1 wherein said reaction is achieved by contacting a mixture of said acyl cyanides, a phase transfer catalyst and a water immiscible solvent with an aqueous solution of said alkali metal borohydride.

6. The method of claim 5 wherein said phase transfer catalyst is tetra-n-butyl ammonium bromide.

7. The method of claim 6 wherein said water-immiscible solvent is methylene chloride.

8. A process for preparing cyanohydrin esters which comprises forming a mixture of an acyl cyanide represented by the structural formula:

$$R_1-\overset{O}{\underset{\|}{C}}-CN,$$

an acyl cyanide represented by the structural formula:

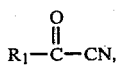

wherein $R_1$ and $R_2$ can be the same or different and each represents an alkyl, alkenyl, cycloalky, diphenyl ether, polyphenyl ether radical or a radical made up of any combination thereof, having a total number of carbon atoms ranging from 1 to about 30; a phase transfer catalyst and a water-immiscible solvent, wherein the total amount of said acyl cyanides in said mixture ranges from about 5% to about 50% by weight mixture and the total amount of said phase transfer catalyst ranges from about 0.005% to about 1.0% by weight of said water-immiscible solvent; bringing said mixture into contact with an aqueous solution of an alkali metal borohydride and maintaining said contact at a temperature and for a time sufficient to convert at least a portion of said acyl cyanides to the cyanohydrin ester product of said acyl cyanides.

9. A process for preparing an insecticidally-active cyanohydrin ester which comprises reacting a mixture of meta-phenoxybenzoyl cyanide and 3-(2,2-dichlorovinyl)-2,2-dimethyl cyclopropane carboxylic acid cyanide with sodium borohydride by a phase transfer reaction in the presence of a phase transfer catalyst to form a cyanohydrin ester product of said meta-phenoxybenzoyl cyanide and 3-(2,2-dichlorovinyl)-2,2-dimethyl cyclopropane carboxylic acid cyanide.

* * * * *